(12) United States Patent
Dalmia et al.

(10) Patent No.: US 8,075,752 B2
(45) Date of Patent: Dec. 13, 2011

(54) METHOD AND APPARATUS FOR PROVIDING AN ELECTROCHEMICAL SENSOR AT AN ELEVATED TEMPERATURE

(75) Inventors: Avinash Dalmia, Hamden, CT (US); Mario Carozza, Danbury, CT (US); Michael J. Rafa, Weston, CT (US); Donald L. Groeschner, New Milford, CT (US); John T. McCaffrey, Avon, CT (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 1141 days.

(21) Appl. No.: 11/353,566

(22) Filed: Feb. 14, 2006

(65) Prior Publication Data

US 2006/0180466 A1     Aug. 17, 2006

Related U.S. Application Data

(60) Provisional application No. 60/653,023, filed on Feb. 15, 2005.

(51) Int. Cl.
*G01N 27/407* (2006.01)
*G01N 27/403* (2006.01)

(52) U.S. Cl. ......... 204/408; 204/417; 204/424; 205/775

(58) Field of Classification Search .......... 204/400–435; 205/775–794.5
See application file for complete search history.

(56) References Cited

U.S. PATENT DOCUMENTS

| | | | |
|---|---|---|---|
| 5,560,810 A * | 10/1996 | Capetanopolous et al. .. | 204/408 |
| 5,844,123 A * | 12/1998 | Marsh et al. ................. | 73/19.12 |
| 6,592,732 B1 * | 7/2003 | Komachiya et al. .......... | 204/426 |
| 2002/0079236 A1 | 6/2002 | Hurland et al. ............. | 205/786.5 |
| 2003/0075443 A1 * | 4/2003 | Dalmia et al. ................. | 204/426 |
| 2003/0085125 A1 * | 5/2003 | Prohaska et al. .............. | 204/424 |
| 2003/0155241 A1 | 8/2003 | Lai et al. ...................... | 204/461 |
| 2005/0147500 A1 * | 7/2005 | Sauciuc et al. ................. | 417/52 |

FOREIGN PATENT DOCUMENTS

| | | |
|---|---|---|
| EP | 0 239 297 | 9/1987 |
| EP | 1 304 565 | 4/2003 |
| JP | 07-095053 | * 10/1995 |
| WO | WO02/077641 | 10/2002 |

OTHER PUBLICATIONS

Thermoelectric Design LLC; Peltier Device Information Directory (http://www.peltier-info.com/info.html); 8 pages.
International Search Report and Written Opinion; May 31, 2006; 10 pages.

* cited by examiner

*Primary Examiner* — Alex Noguerola
*Assistant Examiner* — Gurpreet Kaur
(74) *Attorney, Agent, or Firm* — St. Onge Steward Johnston & Reens LLC

(57) ABSTRACT

The invention relates to an electrochemical sensor and method for providing the sensor having an insulator, an electrode deposited on the insulator, an electrolytic material in contact with the electrode for providing an electrical connection, and a cooling and heating element in contact with the insulator and spaced apart from the electrode for adjusting a temperature of the sensor.

18 Claims, 13 Drawing Sheets

METHOD AND APPARATUS FOR PROVIDING AN ELECTROCHEMICAL SENSOR AT AN ELEVATED TEMPERATURE

CROSS-REFERENCE TO RELATED APPLICATIONS

The present application claims the benefit of, under Title 35, United States Code, Section 119(e), U.S. Provisional Patent Application No. 60/653,023 filed on Feb. 15, 2005, the contents of which are herein incorporated by reference in their entirety.

FIELD OF THE INVENTION

The invention relates to an electrochemical sensor for use at higher temperatures.

BACKGROUND OF THE INVENTION

Monitoring toxic gases is a concern in relation to environmental pollution, occupational health, and industrial emission control. Known methods and apparatuses have been developed to detect the presence of gas. For example, gas chromatography, ion chromatography, electrolytic conductivity detection, and conductometric measurement are typically used to detect gas. However, these manners for detecting gas have generally been expensive, cumbersome, shown to have poor sensitivity and slow response times. They also typically cannot readily be used for on-line measurements. Other manners for monitoring include capacitance sensors and surface acoustic wave sensors. However, the sensitivities, or detection capabilities, of these devices generally fall in the range of low-ppm to high-ppb. Electrochemical sensors were provided to overcome these limitations. Electrochemical sensors typically operate at room temperature, provide a signal which varies with concentrations of analyte species, have short response time, and exhibit acceptable sensitivity, stability, and reproducibility. In addition, electrochemical sensors are compact and can be used for continuous monitoring.

Electrochemical gas sensors usually detect the presence of gases with sufficient reliability and accuracy. However, if the humidity of the sample gas to be measured within the sensor is different than the humidity of the atmosphere surrounding the sensor, which is typically used to determine the baseline of the measurement, a sensor's accuracy may be compromised. The greater the difference in humidity, the less likely the sensor will accurately detect a gas.

In addition, raising a temperature of the sensor may negatively affect its accuracy. At elevated temperatures, which may be any temperature above room temperature, sensors are believed to lose ionic conductivity due to dehydration, which generally worsens over time and which may include dehydration of the electrolytic material, electrolyte solution, or both. Without adequate hydration, the accuracy of measurements taken across the sensing electrode may be compromised. Although the sensor may be refilled with electrolyte or solution to correct the problem, the process may need to be repeated numerous times and, due to the repeated interruptions of the experiment and increased human intervention, this may compound the problem.

In some cases, a low temperature of a sensor may also negatively affect accuracy. A lower temperature may cause the electrolyte to freeze the flow of ions through the electrolyte or electrolytic material to be hampered. As a result, the response of the sensor may not be consistent with sensor readings at room temperature.

SUMMARY OF THE INVENTION

It is, therefore, an object of the invention to provide a sensor and method that provides accurate and consistent readings over time, regardless of ambient conditions.

Another object is to provide a sensor and method that automatically adjust internal temperature independent of the surrounding conditions.

A further object is to provide a sensor and method that promotes hydration of the electrolytic material to maintain sensor sensitivity.

These and other objects of the invention are achieved by an electrochemical sensor having an insulator, an electrode deposited on the insulator, an electrolytic material in contact with the electrode for providing an electrical connection, and a cooling and heating element in contact with the insulator and spaced apart from the electrode for adjusting a temperature of the sensor.

In some embodiments, the insulator is placed between the electrode and cooling and heating element. In embodiments, the insulator is a substrate and may include a hole, where the cooling and heating element is placed in the hole. In some embodiments, the insulator includes a sensor chip for covering the cooling and heating element.

In embodiments, the sensor chip or insulator has a thickness sized to inhibit electrical communication between the electrode and the cooling and heating element.

The sensor can include a reservoir containing electrolyte solution in contact with the electrolytic material for hydrating the electrolytic material.

Optionally, the cooling and heating element further includes a signal receiver for receiving a signal from a temperature controller.

Although preferred but not required, a heat sink can be placed in communication with the cooling and heating element for removing heat from the cooling and heating element. In some of these embodiments, an exhaust is in communication with the heat sink for exhausting the heat. In embodiments, a conductor is provided for dissipating energy from the cooling and heating element.

In an embodiment, the electrolytic material includes an opening extending from a first surface to a second surface of the electrolytic material. In some variations of this embodiment, the opening is proximate to the electrode so that a gas in the opening simultaneously contacts the electrode and the electrolytic material.

In an embodiment, the insulator further includes at least one hole extending from a first surface to a second surface of the insulator for permitting moisture to diffuse through the at least one hole to contact the electrolytic material. In some variations of this embodiment, a reservoir is located on a side of the insulator opposite of the electrolytic material.

In an embodiment, the electrolytic material is spaced apart from the insulator and the electrode is placed between and in contact with both the insulator and electrolytic material. In some variations, the insulator includes a notch for defining a passage for a gas to simultaneously contact the notch, electrode, and electrolytic material.

In another aspect, the electrochemical sensor includes an insulator having a first surface and a second surface, an electrode deposited on the first surface, an electrolytic material in contact with the electrode for providing an electrical connection, a cooling and heating element placed on a side of the second surface for adjusting a temperature of the sensor, and a conductor between the cooling and heating element and the second surface for dissipating energy from the cooling and heating element, wherein the cooling and heating element facilitates hydration of the electrolyte material and adjusts the temperature of the sensor.

In another aspect of the invention, a method for providing an electrochemical sensor includes providing an insulator, depositing an electrode on the insulator, placing an electrolytic material in contact with the electrode for providing an electrical connection, placing a cooling and heating element in contact with the insulator and spaced apart from the electrode, and adjusting a temperature of the sensor with the cooling and heating element.

In some embodiments, the method further includes placing a cooling and heating element in a hole located in the insulator. In embodiments, the method includes placing a heat sink in communication with the cooling and heating element for removing heat from the sensor.

DETAILED DESCRIPTION OF THE ILLUSTRATED EMBODIMENTS

Figure 1:
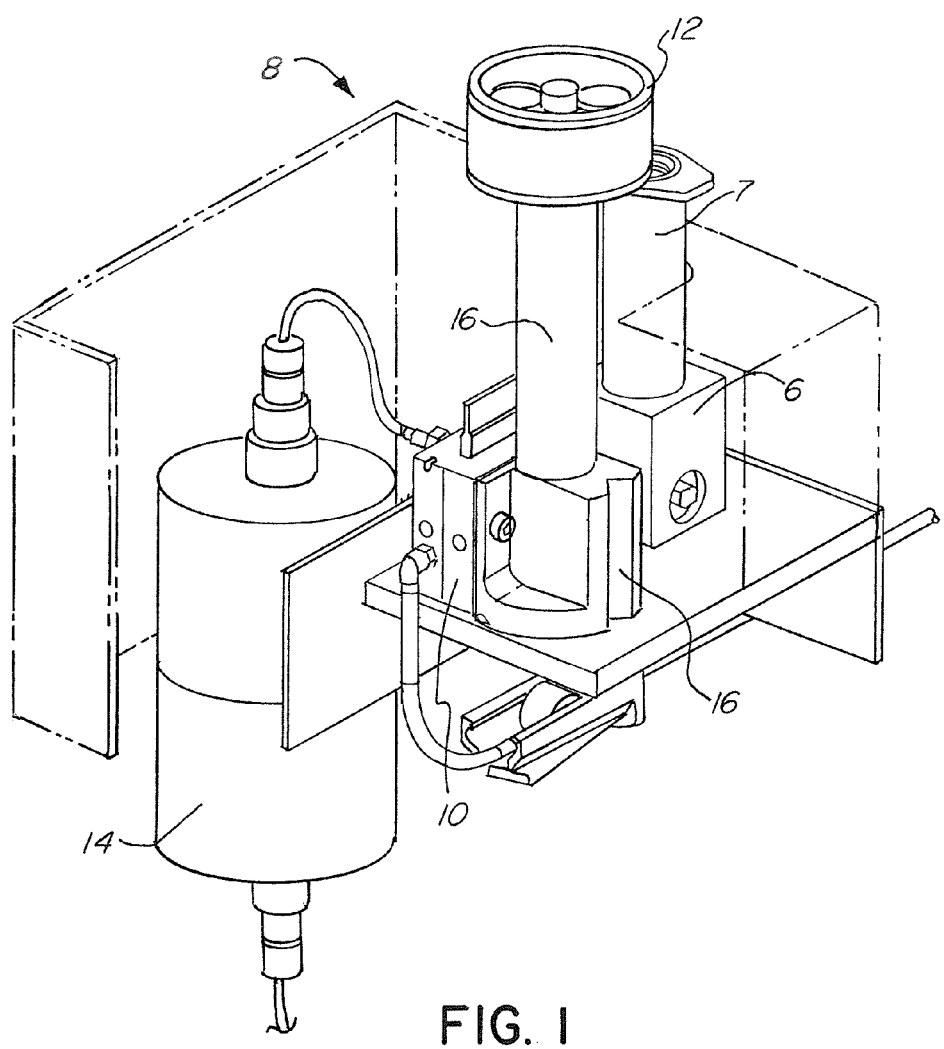
FIG. 1 depicts an apparatus for an electrochemical sensor in accordance with one embodiment of the invention.

FIG. 1 depicts sensing apparatus 8 in accordance with one embodiment of the invention. As shown, sensor 10 is for analyzing samples of gas to detect select gas components within the samples. Reactor 14 is for heating a reactant that may be added to a sample gas within sensor 10, where the heated reactant may enhance detection of a component within the sample gas. Reservoir 6 contains solution, such as electrolyte, to hydrate the electrolytic material within the sensor, where hydration is often needed to enhance accurate detection of the gas component. Electrolyte is supplied to reservoir 6 through supply tube 7.

As shown, reactor 14 is in close proximity to sensor 10, which is usually because practicality dictates the placement of reactor 14 near sensor 10. A disadvantage of reactor 14 being in such close proximity is that heat from reactor 14 may increase a temperature of sensor 10.

Figure 2:
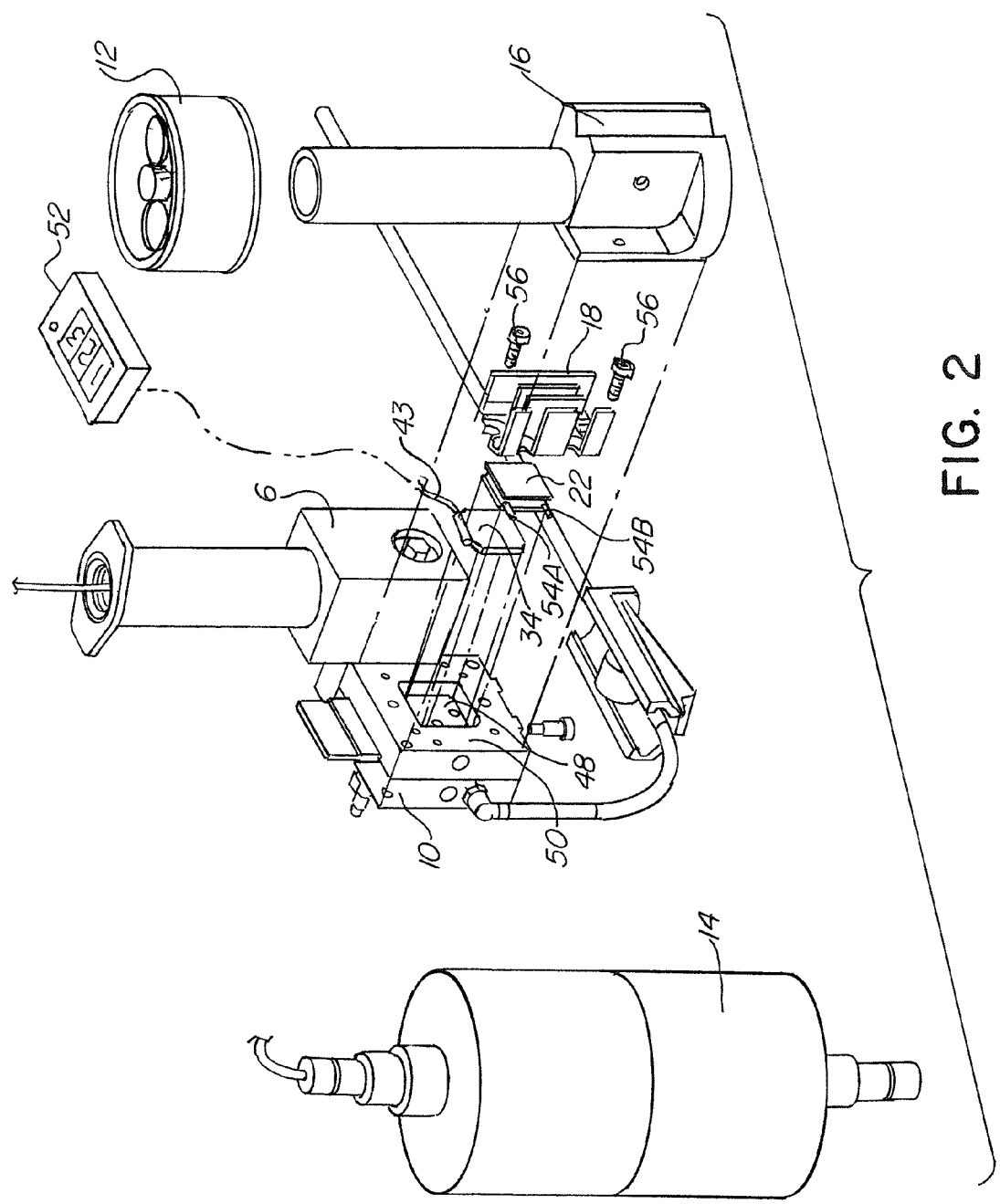
FIG. 2 depicts an assembly view of a sensor according to FIG. 1.

Referring to FIGS. 1 and 2, vent 16 is in close proximity or in contact with sensor 10 for venting heat away from sensor 10, particularly heat sink 18. Vent 16 may optionally include fan 12 or blower for enhancing heat removal away from heat sink 18 by convection. Fan 12 causes a flow of air to be passed over heat sink 18 and out of vent 16 into the atmosphere.

Additionally, as depicted in FIG. 2, element 22 is placed within hole 48, which is usually cut into housing 50 of sensor 10. The material for housing 50 is usually the same as the material for substrate 52 or insulator 20. As shown, element 22 includes electrical leads 54A, 54B so that electrical power may be supplied to element 22. Fasteners 56 are used to secure heat sink 18, element 22, and conductor 34 to housing 50 of sensor 10.

Figure 3:
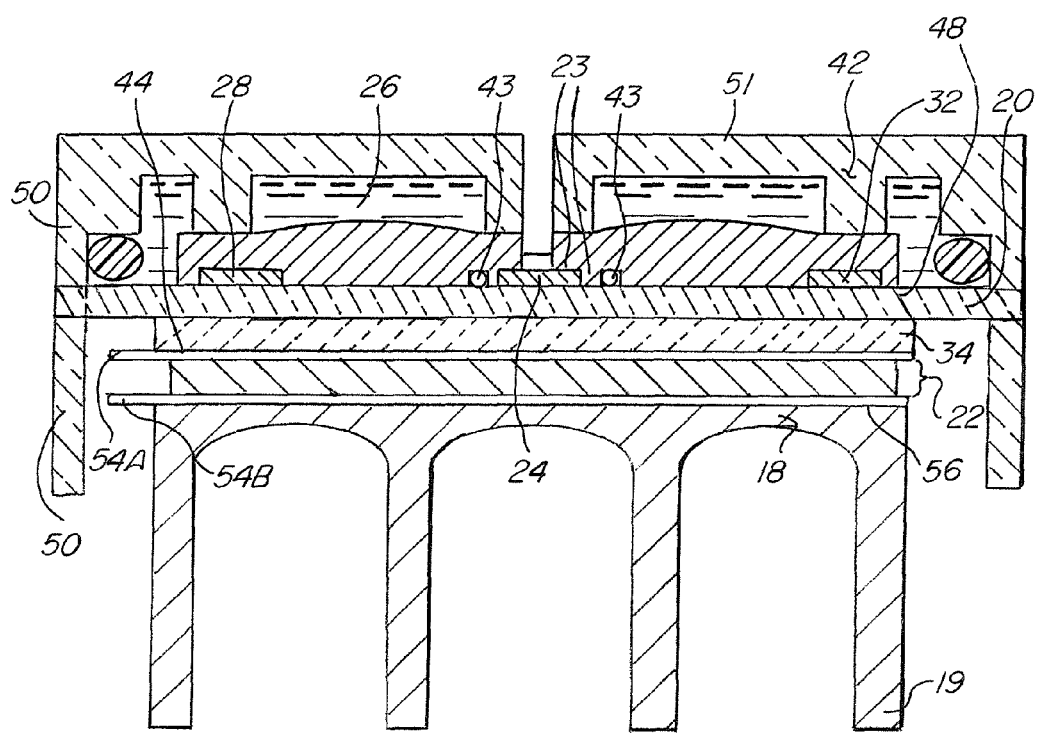
FIG. 3 depicts a cross sectional view of a sensor according to FIG. 1.

As more particularly shown in FIG. 3, sensor 10 includes insulator 20, electrode 24 deposited on insulator 20, electrolytic material 26 in contact with electrode 24 (NOTE: FIG. 3 DOES NOT INCLUDE A "24") for providing an electrical connection from electrode 24 to reference electrode 28 and/or counter electrode 32, and cooling and heating element 22 for helping maintain a temperature within sensor 10. In this effort, conductor 34 and heat sink 18 are employed, although it is understood that element 22 may operate properly without conductor 34 or heat sink 18. Conductor 34 and heat sink 18 function to enhance efficiency of dissipating heat or coldness.

For example, when reactor 14 gives off heat and causes the temperature of sensor 10 to rise, element 22 operates as a cooling element by taking heat away from interior 42 (NOTE: FIG. 3 DOES NOT INCLUDE A "42") of sensor 10. Heat from interior 42 would transfer to conductor 34, which then transfers the heat to heat sink 18. Heat sink 18, and fins 19 of heat sink 18, dissipate the heat into vent 16.

As shown, cooling and heating element 22 is a peltier cooler/heater. In other embodiments, another device capable of cooling or heating sensor may be used. In embodiments, element 22 is additionally and/or optionally a cooling device. By incorporating cooling and heating element 22, the internal temperature of sensor 10 can be maintained in a desired range, for example in the illustrated embodiments, a range of 20-25° C., despite radiation from reactor 14 and ambient conditions, which in the illustrated embodiment may be above 30° C.

Although a user may fill reservoir 7 with electrolyte via supply line 7 in order to hydrate sensor 8, this process may need to be repeated on a frequent basis without element 22. Such repetition may interrupt experiments and, due to the interruptions, cause inaccurate readings. Further, this continual replenishment may simulate a back and forth dehydrating and hydrating cycle and may not be as effective as element 22 being placed within sensor 10 to help maintain a consistent temperature. In addition, repeated dehydration to a sensor may cause damage to the sensor, regardless whether or not the sensor is subsequently hydrated.

Without element 22 to adjust a temperature of sensor 10, experimental data suggests the response of sensor 10 may vary by approximately 5-10% per 1° C. change in temperature. The greater the change in temperature, the greater the sensor variation and, therefore, the greater the error. Placing element 22 in sensor 10, and more specifically at or near electrode/electrolytic material interface 23, so that the internal temperature may be held at a generally consistent temperature can reduce sensor and/or measurement error. Although response readings may be taken when the temperature inside sensor 10 is in the range of approximately 10-35° C., response readings when the internal temperature is in the range of approximately 15-30° C. were preferred in the illustrated embodiment.

So that element 22 is activated when the temperature of sensor 10 rises, thermocouple 43 may be placed in sensor 10 at a variety of locations, or, in the illustrated embodiment, near interface 23. In some embodiments, temperature controller 52 is connected to thermocouple 43 to read and/or display the temperature of thermocouple 43. Temperature controller 52 is also in communication with element 22 for controlling or instructing element 22 to provide coldness or warmth to sensor 10 based on the readings of thermocouple 43. In some embodiments, temperature controller 52 is a thermostat, computer, processor, or other device for enabling element 22 to help maintain a generally consistent temperature within sensor 10 automatically and without further user intervention. As shown, signal receiver 54 located on element 22 can receive a signal, such as an electrical signal, from temperature controller 52. Signal receiver 54 has the same features as temperature controller 52, including leads 54A, 54B.

When ambient temperature, or temperatures outside sensor 10, either rises above 30° C. or goes below 15° C., the internal temperature begins to rise or fall, respectively. When reactor 14 is utilized in close proximity to sensor 10, and when normal operating temperatures of reactor 14 are usually in the range of approximately 800-1200° C., sensor 10 may be inadvertently heated due to radiation and convection from reactor 14. The effects due to reactor 14 are in addition to or instead of the effects due to ambient conditions. As explained above, such effects are believed to cause dehydration that results in sensor signal degradation and lower response stability. Element 22 may thus assist in maintaining the internal temperature in the range of approximately 15-30° C. regardless of the ambient conditions.

Figure 4:
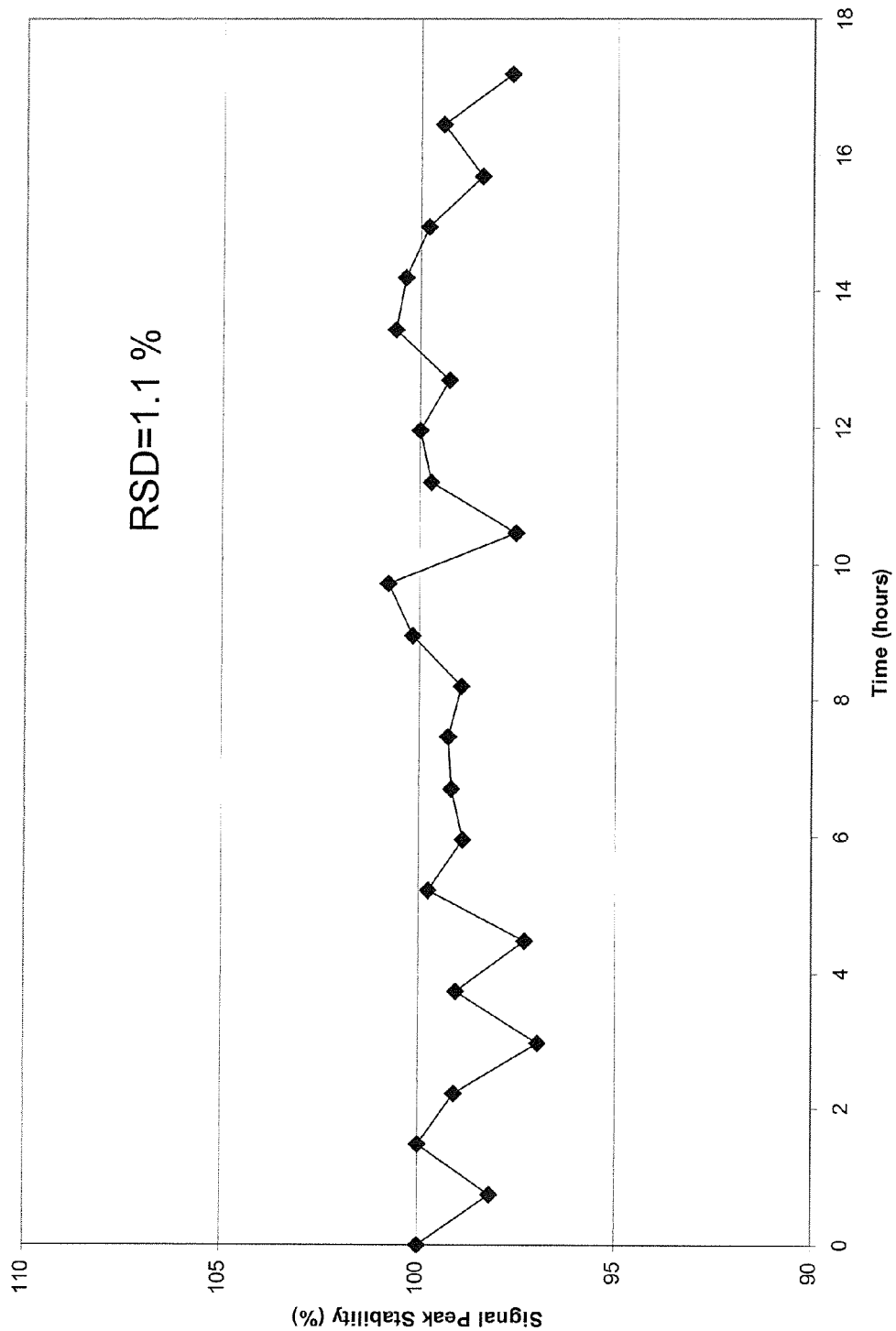
FIG. 4 depicts stability of response readings over time for a sensor according to FIG. 1.

FIG. 4 shows the stability of the signal using a sensor with element 22 over time for an experiment of a sample gas containing 300 ppb DMS (di-methyl sulfide) in Helium. The experiment also used a 0.32 mm ID RTX-1 column in gas chromatography for sample separation and a reactor for conversion of DMS to $H_2S$. The temperature was approximately room temperature.

As shown, the relative standard deviation (RSD) of the signal was about 1.1% over 17 hours, which is low as compared to RSD of the signal obtained without element 22. In fact, the stability shown is about 4-10 times lower the same experiment without element 22. Hence, the sensor response is more stable with sensor cells having element 22 at room temperature.

Figure 5:
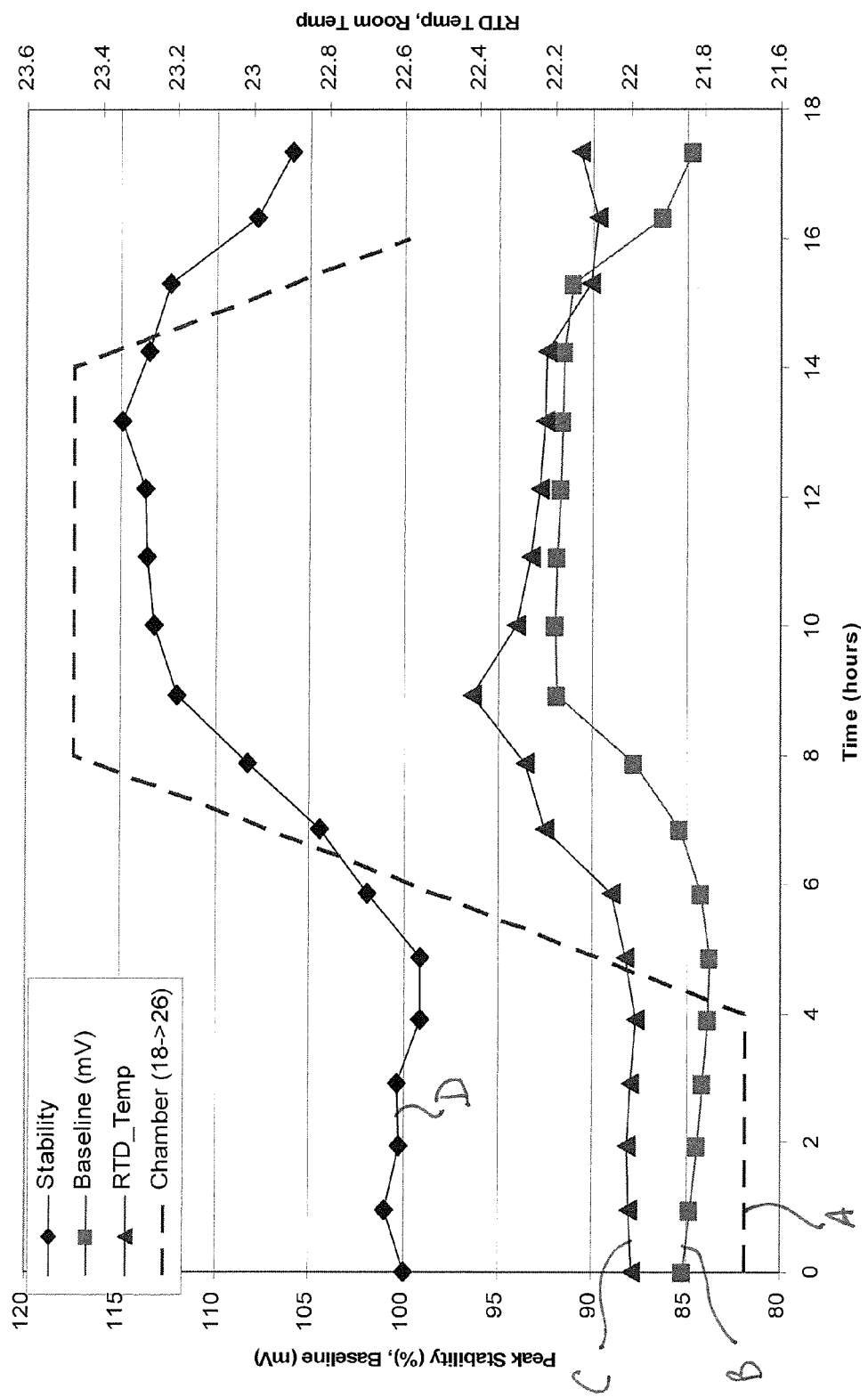
FIG. 5 depicts stability of response readings over time for various areas of a sensor according to FIG. 1.

FIG. 5 depicts a comparison between sensor readings with and without element 22 during an experiment where ambient temperature changed from approximately 18 to 26° C. Line A shows the temperature of the atmosphere, or ambient, surrounding sensor 10. As shown, the stability of line A over time varies according to the temperature. In other words, stability is dependent upon ambient conditions.

Line B represents a baseline of sensor 10 where there is no analyte being measured. Line C represents a thermocouple temperature located within sensor 10. Line D represents a sensor signal when analyte is within sensor 10.

As shown, element 22 reduces the dependence of sensor response and baseline on ambient temperatures. The sensor signal and baseline changes (lines B-D) by approximately 1.5% and 1 mV per ° C., respectively. The response and baseline changes are reduced by a factor of approximately 3-5 and 5-20, respectively, in comparison to a system without element 22 (line A).

As shown in FIG. 3, cooling and heating element 22 is placed within sensor 10 to help maintain a consistent desirable temperature within sensor 10 and, as a result, help maintain hydration of electrolytic material 26. Element 22 is shown to be spaced apart from electrode 24 so that electrical conductivity between element 22 and electrode 24 is reduced. To further reduce electrical conductivity between element 22 and electrode 24, which may cause a short circuit within sensor 10 or interference in accurate readings of sensor 10, insulator 20 is placed between electrode 24 and element 22. In other embodiments, element 22 is placed above electrode 24, such as being contained within top 51 of the housing (see FIGS. 3, 7, 10, 12, and 13).

As shown in FIG. 3, hole 48 is cut into substrate 52 or housing 50, where hole 48 does not penetrate all the way through substrate 52 so that there is an insulative space between element 22 and electrode 24. In the event hole 48 penetrates all the way through substrate 52, a substrate chip or insulator 20 may be inserted into hole 48 and electrode 24 can be deposited upon chip 20. It is understood insulator 20 may be one or more of many insulative materials between electrode 24 and element 22, including being the sensor chip, substrate 52, housing 50, and the like.

As shown, conductor 34 is in contact with insulator 20 for transferring heat from insulator 20 and, indirectly, other components of sensor 10 such as electrode 24, electrolytic material 26, and interior space 42. Heat is transferred from conductor 34 to element 22 and to heat sink 18, where it is vented to vent 16.

Although element 22 is used to offset the heating effects from reactor 14 by cooling sensor 10, it is understood that element 22 is capable of heating sensor 10 in the event sensor 10 is subjected to conditions that may cause the temperature of sensor 10 to be lower than desired. Element 22 then provides heat to sensor 10 to help maintain a consistent temperature.

In this effort, the direction of travel for energy of element 22 is reversed. In other words, heat travels from bottom surface 56 of element 22 toward top surface 44. Upon the energy or heat reaching top surface 44, it is transferred to conductor 34 where it is dissipated into sensor 10.

Figure 6:
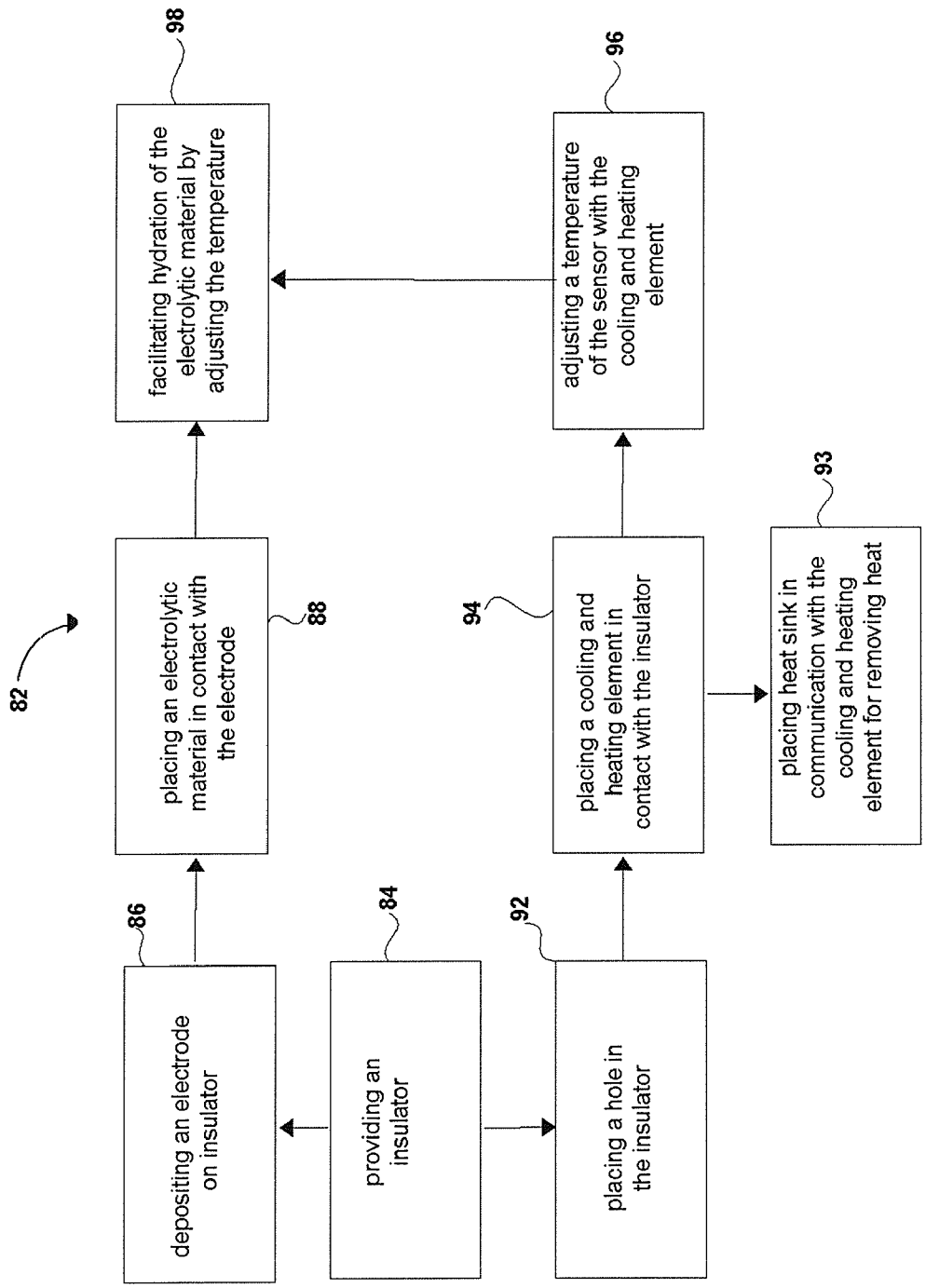
FIG. 6 depicts a method for providing a sensor according to FIG. 1.

FIG. 6 depicts method 82 for providing sensor 10 in accordance with one embodiment of the invention. Method 82 includes the steps of providing 84 an insulator, depositing 86 an electrode on the insulator, placing 88 an electrolytic material in contact with the electrode, placing 94 a cooling and heating element in contact with the insulator, adjusting 96 a temperature of the sensor with the cooling and heating element, and facilitating 98 hydration of the electrolytic material by adjusting the temperature of the sensor.

Optionally, method 82 may also include placing 92 a hole in the insulator for placement of the cooling and heating element within the hole. Method 82 may also include placing 93 a heat sink in communication with the cooling and heating element for removing heat.

Figure 7:
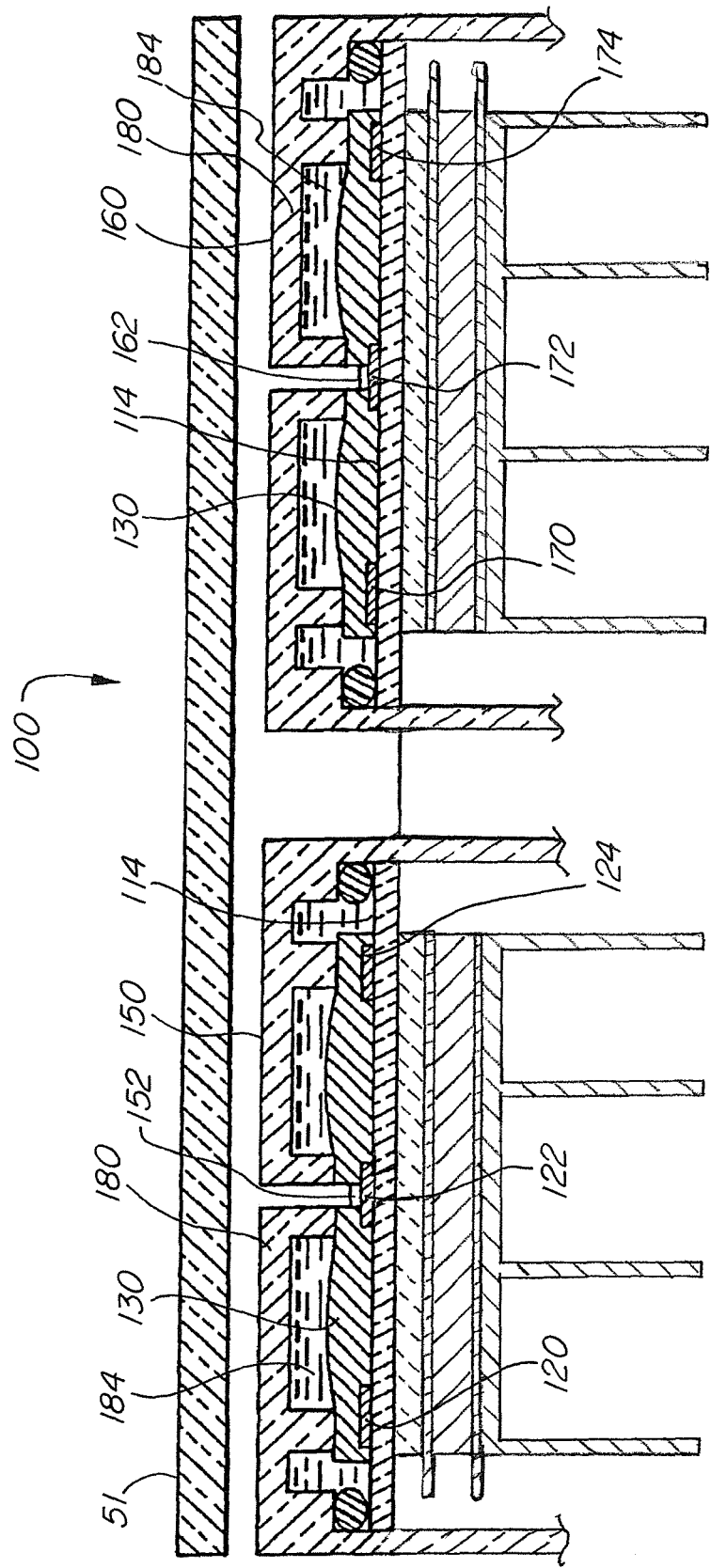
FIG. 7 depicts another embodiment of a sensor according to FIG. 1.

FIG. 7 depicts another embodiment of an electrochemical gas sensor 100 in accordance with the invention. Electrochemical gas sensor 100 comprises two sensors, reference sensor 150 and active sensor 160, each of which is constructed the same and has the same features as the other except for having different thicknesses of electrolytic material 152 and 162 on the sensing electrodes. Both reference and active sensors include a housing, a substrate, a surface of the substrate for depositing electrodes thereon, electrolytic material for carrying ions between the electrodes, a first electrode, and a second electrode. Electrochemical gas sensor 100 operates to detect the presence of a particular gas while compensating for relative humidity by wetting the electrolytic material to reduce humidity dependence. Sensor 100 further compensates for relative humidity without directly measuring it.

Sensor 100 detects the presence of a desired gas in an unknown mixture of gases by taking the difference between a measurement of current between first and second electrodes, 120 and 122, of reference sensor 150 and a measurement of current between first and second electrodes, 170 and 172, of active sensor 160. The measurement of current is indicative of the concentration of a gas present. Electrolytic material 130 is in contact with both first and second electrodes of each sensor and acts as a conductive medium to carry ions from the first electrode to the second electrode, or vice versa. Reservoir 180 contains solution 184 for wetting electrolytic material 130.

As depicted in FIG. 7, first electrode 120 is the counter electrode and second electrode 122 is the sensing or working electrode. However, first and second electrodes, 120 and 122, are interchangeable and second electrode 122 may be the counter electrode whereas first electrode 120 may be the sensing electrode. The same is true of first and second electrodes, 170 and 172, of active sensor 160.

First electrode 120 and second electrode 122 may include a conductive material suitable for conducting electricity. Generally, a metallic material, such as Platinum, may be used but other materials permitting a measurement of current between the electrodes suffice. The electrodes are deposited using thin film techniques, including spin/sputter coating or evaporating the electrodes onto surface 114. Besides spin/sputter coating, the electrodes may also be deposited using photolithography.

In addition, reference sensor 150 and active sensor 160 may each include a third electrode 124, 174 deposited on surface 114. Third electrode 124 on reference sensor 150 and third electrode 174 on active sensor are not necessary for functioning of electrochemical gas sensor 100 but may improve sensitivity, accuracy, selectivity, and/or repeatability. Third electrodes 124 and 174, acting as reference electrodes, provide a stable reference potential for setting the sensing electrode potential at which the current between the counter and sensing electrodes is measured with higher reproducibility and stability. The third electrodes, or reference electrodes, include all the features of both the first and second electrodes and may further be interchanged with either of them. However, for the purposes of FIG. 7, third electrodes 124 and 174 are depicted as the reference electrodes.

Figure 8:
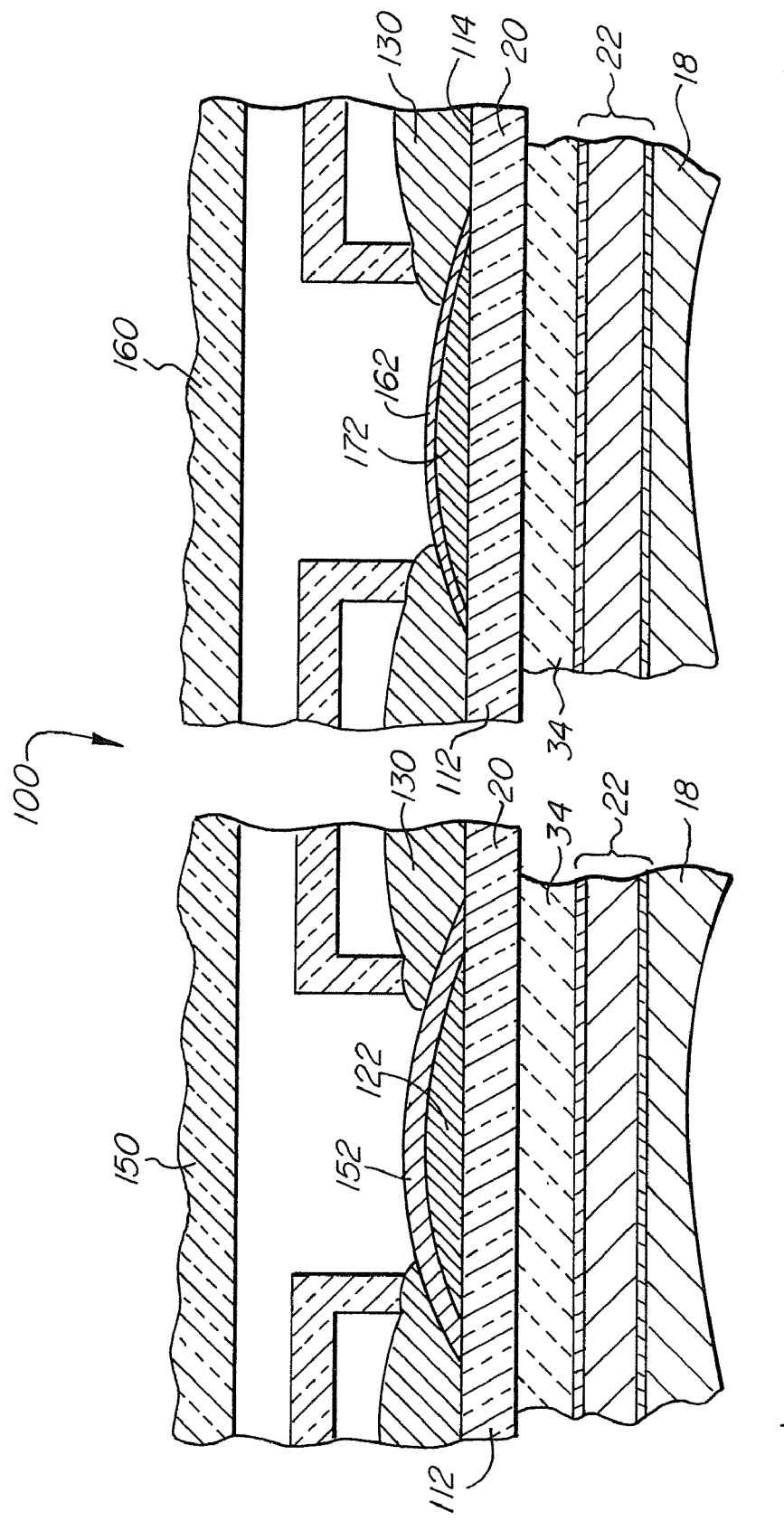
FIG. 8 more particularly depicts the electrode shown in FIG. 7.

As shown in FIG. 8, electrolytic material 130 further includes thin-film 162 of a conductive medium in contact with the sensing electrode of active sensor 160 and thin layer 152 of a conductive medium in contact with the sensing electrode of reference sensor 150. Thin film 162 and thin layer 152 may improve sensitivity because they increase the contact areas between the gas, electrolytic material 130, and electrodes. Moreover, because thin film 162 and thin layer 152 have thicknesses less than electrolytic material 130, response time and gas diffusion is enhanced. Thin film 162 and thin layer 152 are made of the same material as electrolytic material 130 or any ion conductive material.

Where the humidity of the gas being measured is different than the humidity of the atmosphere surrounding sensor 100, a measurement of current may provide inaccurate indications as to the concentration of the gas because humidity affects current measurements. Furthermore, because humidity cannot be controlled by sensor 100, sensor 100 compensates for relative humidity without measuring the humidity directly. Hence, sensor 100 can reduce the uncertainty, or error, when compensating for relative humidity because the humidity is not being measured.

Sensor 100 compensates for relative humidity without directly measuring the humidity by having thin layer 152 of electrolytic material on sensing electrode 122 of reference sensor 150 being of a different thickness than film 162 of electrolytic material 130 on sensing electrode 172 of active sensor 160. This is more particularly depicted in FIG. 8. Because gas diffuses through electrolytic material 130, and more particularly layer 152 and film 162, in order to be detected, varying the thickness of electrolytic material 130 affects the amplitude of the response signal of sensor 100. Following this concept, the illustrated embodiments utilize the effect on the amplitude of the response signal to provide a mathematical determination of the detected gas compensated for relative humidity. Moreover, the mathematical determination is desirably independent of a measurement of relative humidity. Using hydrogen disulfide as an example of gas to be detected and where layer 152 is 10 times thicker than film 162, the mathematical determination is as follows:

Sensor 1 (thin Nafion coating):  100% $H_2S + RH_1 - RH_2$

Sensor 2 (10 times thicker Nafion coating):  10% $H_2S + RH_1 - RH_2$

Differential measurement(Sensor 1 − Sensor 2):  90% $H_2S$ $RH_1$ is the relative humidity of the sample gas and $RH_2$ is the relative humidity of the surrounding air or gas used for baseline measurement. Because humidity is not being measured, the invention, therefore, reduces error associated with a humidity measurement. As shown in FIG. 7, layer 152 is approximately between 2.5 and 130 micrometers thick. Film 162, being 10 times thinner, is approximately between 0.25 and 3 micrometers thick.

So long as layer 152 and film 162 are of different thickness, sensor 100 detects the presence of a gas while compensating for the relative humidity. Preferably, but not necessary for proper function of sensor 100, layer 152 is at least 10 times thicker than film 162. In another embodiment, layer 152 is 10 times thicker than film 162. Therefore, layer 152 is approximately between 10 and 60 micrometers thick, whereas film 162 is approximately between 0.5 and 3 micrometers thick. The mathematical formula will therefore be as follows:

Sensor 1 (thin Nafion coating):  100% $H_2S + RH_1 - RH_2$

Sensor 2 (20 times thicker Nafion coating):  5% $H_2S + RH_1 - RH_2$

Differential measurement(Sensor 1 − Sensor 2):  95% $H_2S$

In an embodiment, layer 152 is orders of magnitude thicker than film 162 and the mathematical formula will change correspondingly. The reason is that variances in thicknesses between layer 152 and film 162 provide corresponding differences in gas diffusion through electrolytic material 130. This is desirable because as the difference in thickness between layer 152 and film 162 increases, the differential measurement between the active and reference sensors' readings approaches 100%. As the difference in readings approach 100%, the more accurate sensor 100 becomes while compensating for relative humidity, and the lower the standard of deviation and/or error in the readings become. Hence, although a preferred difference in the thicknesses of layer 152 and film 162 is that layer 152 be at least 10 times thicker, any difference in thicknesses suffices. The lower the difference in thicknesses, the greater the standard of deviation and/or error.

Figure 9:
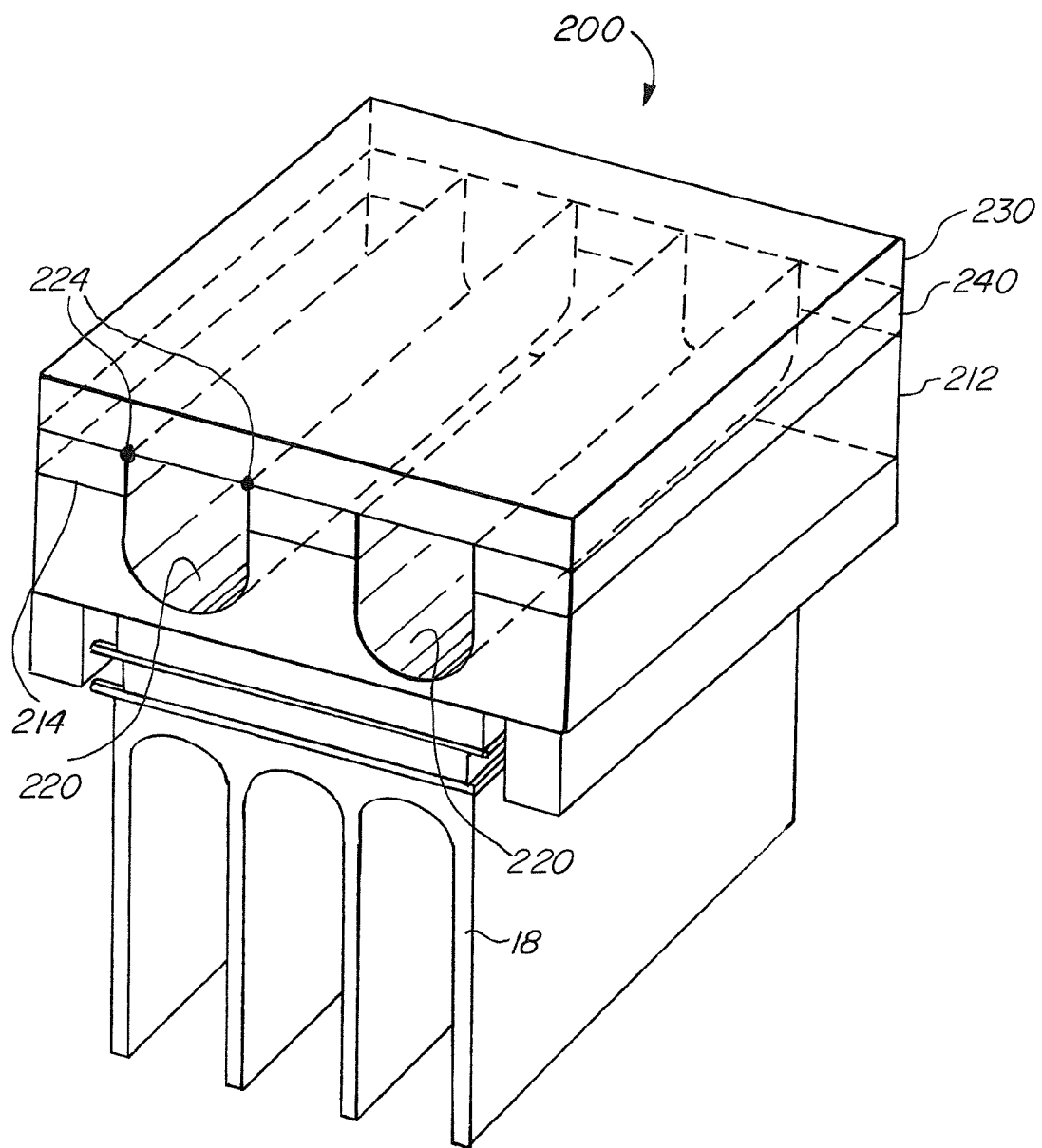
FIG. 9 depicts another embodiment of a sensor according to FIG. 1.

FIG. 9 depicts another embodiment of sensor 200, which includes Notch 220. Notch 220 is an indentation, channel, groove, or etching in substrate 212 or, more specifically, surface 214 for defining a passage for receiving gas. As depicted in FIG. 9, notch 220 is a channel within which gas is transported within electrochemical gas sensor 200 to three-way interface 224 after being received from a gas source or pump. Notch 220 may be formed or manufactured using one or more of many known or novel methods or equipment, such as machining, grinding, etching, laser cutting, or the like.

Each notch further includes electrolytic material 230, and film 240 of conductive material. As shown, film 240 is used to connect notches, thereby permitting electrical measurements to be made as to the amount of gas present in each notch.

Figure 10:
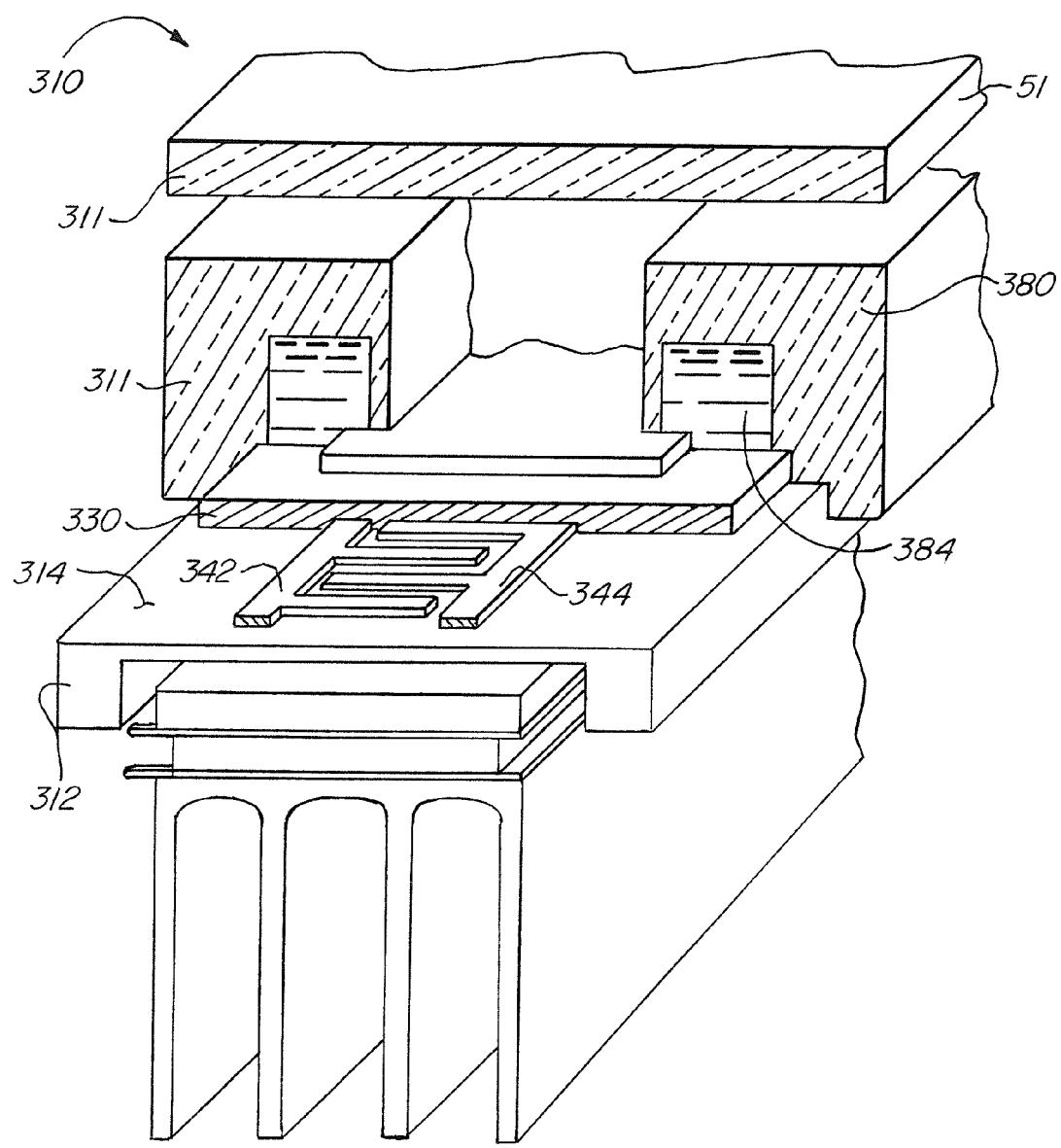
FIG. 10 depicts another embodiment of a sensor according to FIG. 1.

FIG. 10 depicts another embodiment of the invention. Electrochemical gas generator 310 comprises housing 311, substrate 312, surface 314 of substrate 312, electrolyte 330, first electrode 342, and second electrode 344. Electrochemical gas generator 310 operates to generate a known concentration of desired gas.

Substrate 312 includes known or novel materials used for forming a supporting surface 314 upon which the electrodes are placed. The substrate has a surface that is generally, although not necessarily, flat so that a desirably thin film of interdigitated electrodes 40 may be deposited thereon free from unnecessary pores or crevices, thereby reducing wicking and porosity, both of which disadvantageously affect generator sensitivity. Suitable substrate materials include glass or any nonconductive material. Substrate 312 and surface 314 should be made of a material that is a relative poor conductor of electricity so as not to interfere with proper functioning of electrochemical gas generator 310. Such a material may be classified as an insulating material.

Electrolytic material 330 includes a thin film of a conductive medium for use as an electrolyte for carrying a flow of ions or current between first and second electrodes, 342 and 344. Electrolytic material 330 further includes an ionically or electrically conductive medium in the solid state, such as Nafion.

Solution 384 operates to improve the generator's efficiency by wetting electrolytic material 330. Solution 384 includes electrolyte, water, or an acid solution. Solution 384 is contained in reservoir 380 within generator 310. However, a controlled wetting is desired for flooding the electrolytic material causes the electrodes to be flooded. Flooding the electrodes with solution 384 negatively affects sensor response time and accuracy.

Figure 11:
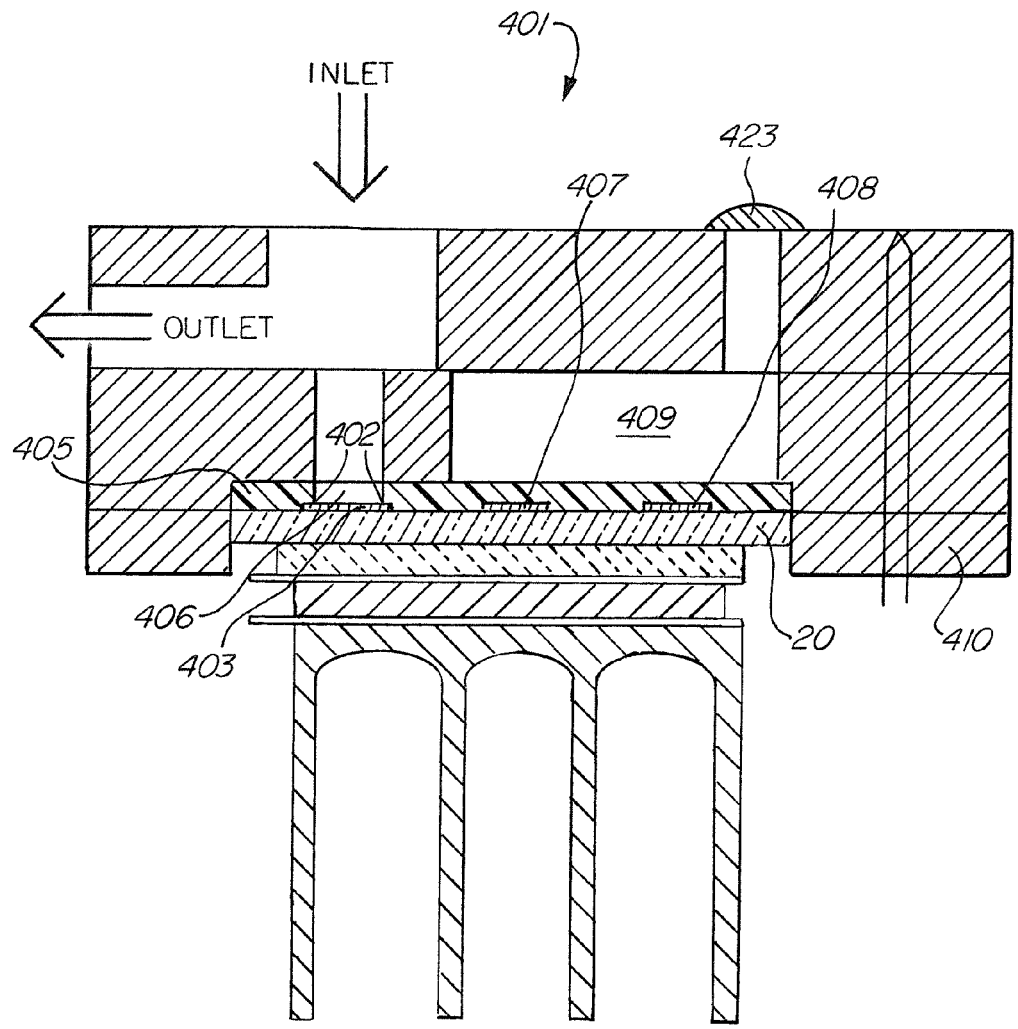
FIG. 11 depicts another embodiment of a sensor according to FIG. 1.

In FIG. 11, the film type sensor cell assembly 401 includes a three-phase contact area 402 for the sensing electrode 403, where the gas sample, the sensing electrode 403, and the solid ionomer membrane 405 can interface as an essential part of the sensor design. The three-phase contact area 402 is formed by openings 406, i.e., of circular shape, about 1.0 mm in diameter, in the solid ionomer membrane 405 over the sensing electrode 403. The sensor's response time is based on the solid ionomer membrane 405 layer acts simply as a proton conducting element between the film type sensing 403, reference 407, and counter 408 electrodes. Signal response is further affected by a special ionomer membrane treatment process which serves to "catalytically activate" the membrane. During this process, platinum is embedded in the solid ionomer membrane 405. The response is due to the fact that the platinum, Pt, incorporated into the membrane 405, contributes to the signal generation in the three-phase contact area 402. The finely dispersed platinum is immobilized within and on the surface of the membrane 405 and does not affect the membrane's 405 ionic conductivity or water content. Also, this finely dispersed catalyst within the membrane 405 catalytically reacts with the permeating gases and to reduce the likelihood of reactive gases reaching the reference electrode 407, and disturbing it from its Pt/air ($O_2$) rest potential.

The film type sensor cell assembly shown in the schematic drawing of FIG. 11 includes a water reservoir 409 to keep the solid ionomer membrane 405 hydrated. The water reservoir 409 is sealed with a cap 423. When using the devices in a humid atmosphere, a water reservoir 409 may not be required and would make the sensor housing design 410 significantly simpler, while the device could be packaged under humidified condition, ready for use.

Figure 12:
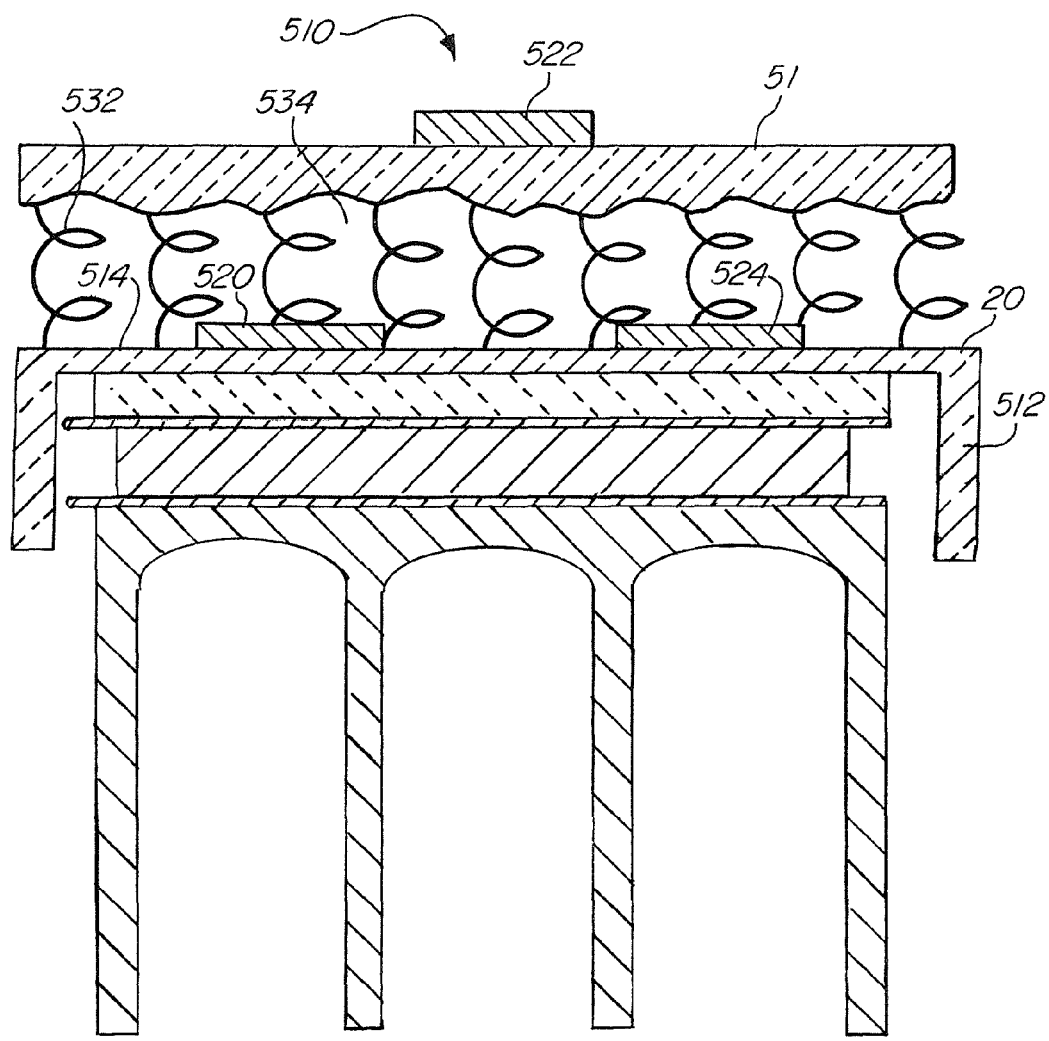
FIG. 12 depicts another embodiment of a sensor according to FIG. 1

FIG. 12 depicts electrochemical gas sensor 510 in accordance with the invention. Electrochemical gas sensor 510 comprises substrate 512, surface 514 of substrate 512, first electrode 520, second electrode 522, and electrolyte having a predetermined porosity. Electrochemical gas sensor 510 may further include third electrode 524.

The electrolytic support layer includes a thin film of an electrically conductive medium 534 for carrying a flow of ions or current between first and second electrodes, 520 and 522. The conductive medium 534 also carries a flow of ions or current between third electrode 524, if applicable, and either first or second electrode. The illustrated electrolytic support layer further includes a plurality of columns 532 formed by a glancing angle deposition ("GLAD") process. The electrolytic support layer formed using the GLAD process produces a film having a predetermined porosity and pore size. Further, electrolytic support layer, being porous and having spaces in between the plurality of columns, acts as a mechanism for holding a conductive medium 534, such as an electrolyte. Electrolytic support layer formed using the GLAD process has a porosity in the range of 5%-50% and a pore size in the range of 0.01-1 microns. Because increased porosity and pore size is desirable for holding electrolyte 534, the electrolytic support layer may have porosity in the range of 5%-80% and a pore size in the range of –2 microns.

Electrolyte 534 may be held in between the columns and within the pores of the electrolytic support layer. Hence, electrolytic support layer formed using the GLAD process is advantageous in that it permits the thickness of the overall electrolytic support layer to be that of a thin film, generally less than 5 micrometers thick or, preferably, less than 2 micrometers thick. Electrolyte 534 will not disperse and run off due to being held by plurality of columns 532. An electrolytic support layer may further include a thin coating 536 or film on first electrode, second electrode, third electrode, or a combination thereof. Because the electrolytic support layer is desirably thin and electrode 522 is deposited on top of the electrolytic support layer, the time for gas to diffuse through it is shortened, thereby enabling electrochemical gas sensor 510 to have a quicker response time and a sensitivity to the sub ppb concentration range whereas conventional sensors generally have detection capabilities in the high ppb to ppm range.

Figure 13:
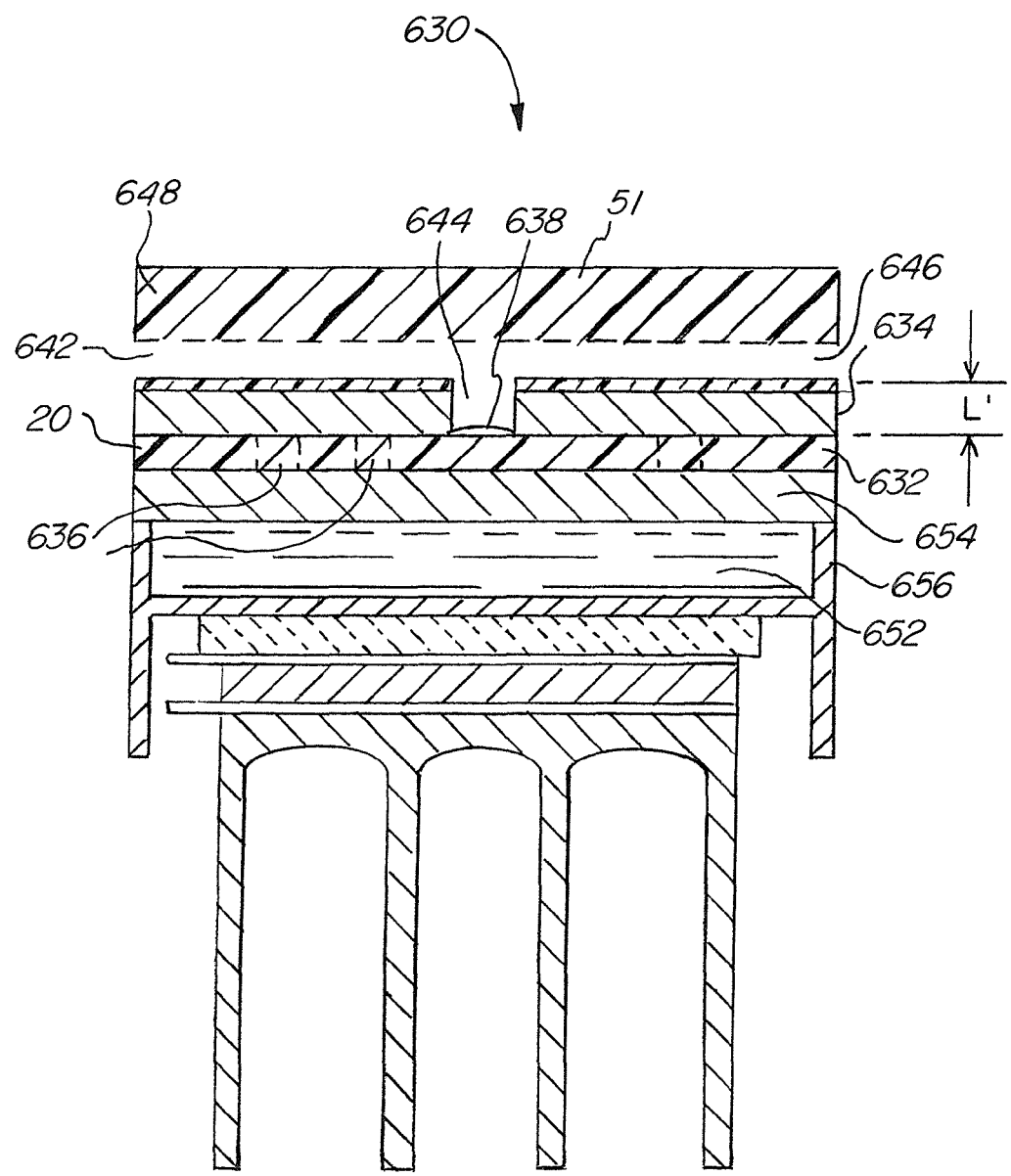
FIG. 13 depicts another embodiment of a sensor according to FIG. 1.

FIG. 13 depicts the electrochemical gas sensor 630 in accordance with the invention. Sensor 630 includes substrate 632, ionomer membrane 634, and electrode 638 placed within housing 648. Gas enters sensor 630 through inlet 642 and is detected after diffusing through diffusion hole 644 to contact electrode 638, which is in contact with ionomer membrane 634. Gas exits sensor 630 through outlet 646. It is understood that the gas may flow in a reversed direction where outlet 646 is the inlet and inlet 642 is the outlet.

Sensor 630 of FIG. 13 overcomes this disadvantage by wetting ionomer membrane 634, via hole 636 in substrate 632, with solution 652 located on a side of substrate 632 opposite from electrode 638. Because of the position of reservoir 656, length L' can be shortened, thereby reducing gas diffusion time and improving the sensitivity of sensor 630. The more length L' is reduced, the faster the response time of sensor 630. In some embodiments, length L' is less than 1.4 mm. In other embodiments, length L' is less than 0.1 mm. In further, embodiments, length L' is less than 0.5 mm. In still further embodiments, length L' is less than 0.1 mm. In fact, length L' or a thickness of ionomer membrane 634 may be reduced until it is flush with or below a surface of electrode 638. In some embodiments, diffusion hole 644 is eliminated because length L' is flush with or below a surface of electrode 638. All that is required is for ionomer membrane 634, of any length L', to be in contact with electrode 638 so that gas entering through inlet 642 provide a desired gas/ionomer membrane/electrode interface.

To further enhance sensitivity, a thickness of substrate 632 is reduced to improve wetting by solution 652. Substrate 632 is of an electrically non-conductive material for providing a surface upon which electrode 638 is placed. Optionally, substrate 632 is a thin foil having insulative, or electrically non-conductive, properties, such as Kapton or any other material. The foil is not metallic or conductive. The foil may also be flexible as compared to ceramic or glass. The thickness of the foil, or substrate 632, is generally less than approximately 4 mils and preferably less than approximately 1 mil. The thinner substrate 632, the faster ionomer membrane 634 is wetted and this positively affects sensor response time. Therefore, as the thickness of substrate 632 approaches 0 mils, the response time is further reduced.

Optionally, in some embodiments, sensor 630 may include wicking material 654 to facilitate or enhance wetting of ionomer membrane 634 by solution 652. Wicking material 654 is typically of a material that absorbs liquid, such as a sponge. Hence, as shown in FIG. 13, wicking material 654 will draw solution 652 upwardly from reservoir 656 toward ionomer membrane 634.

It is understood that sensor 10 is applicable to detecting both gas and liquid samples. Although the invention has been described with reference to particular arrangements of parts, features, and the like, these are not intended to exhaust all possible arrangements or features, and indeed many other modifications and variations will be ascertainable to those of skill in the art.

What is claimed is:

1. An electrochemical sensor, comprising
an insulator, said insulator including a hole;
an electrode deposited on said insulator;
an electrolytic material in contact with said electrode for providing an electrical connection;
a reservoir containing electrolyte solution in contact with said electrolytic material for hydrating said electrolytic material; and
a cooling and heating element placed in said hole in said insulator and spaced apart from said electrode for adjusting a temperature of the sensor, wherein the cooling and heating element is a Peltier cooling and heating element.

2. The sensor according to claim 1, wherein said insulator is placed between said electrode and said cooling and heating element.

3. The sensor according to claim 1, wherein said insulator is a substrate.

4. The sensor according to claim 1, wherein and said insulator includes a sensor chip for covering said cooling and heating element.

5. The sensor according to claim 4, wherein said sensor chip has a thickness sized to inhibit electrical communication between said electrode and said cooling and heating element.

6. The sensor according to claim 1, wherein said cooling and heating element further includes a signal receiver for receiving a signal from a temperature controller.

7. The sensor according to claim 1, further comprising a heat sink in communication with said cooling and heating element for removing heat from said cooling and heating element.

8. The sensor according to claim 7, further comprising an exhaust in communication with said heat sink for exhausting the heat.

9. The sensor according to claim 1, further comprising a conductor for dissipating energy from said cooling and heating element.

10. The sensor according to claim 1, wherein said electrolytic material includes an opening extending from a first surface to a second surface of said electrolytic material.

11. The sensor according to claim 10, wherein said opening is proximate to said electrode so that a gas in said opening simultaneously contacts said electrode and said electrolytic material.

12. The sensor according to claim 10, wherein said insulator further includes at least one hole extending from a first surface to a second surface of said insulator for permitting moisture to diffuse through said at least one hole to contact said electrolytic material.

13. The sensor according to claim 12, further comprising a reservoir located on a side of said insulator opposite said electrolytic material.

14. The sensor according to claim 1, wherein said electrolytic material is spaced apart from said insulator and said electrode is placed between and in contact with both said insulator and said electrolytic material.

15. The sensor according to claim 14, wherein said insulator includes a notch for defining a passage for a gas to simultaneously contact said notch, said electrode, and said electrolytic material.

16. An electrochemical sensor, comprising
an insulator having a first surface and a second surface;
an electrode deposited on said first surface of said insulator;
an electrolytic material in contact with said electrode for providing an electrical connection;
a reservoir containing electrolyte solution in contact with said electrolytic material for hydrating said electrolytic material;
a cooling and heating element placed between said first surface and said second surface of said insulator for adjusting a temperature of the sensor;
a conductor between said cooling and heating element and said second surface for dissipating energy from said cooling and heating element; and
wherein the cooling and heating element is a Peltier cooling and heating element, said cooling and heating element facilitates hydration of said electrolyte material and enhances sensitivity of said electrode by adjusting the temperature of the sensor.

17. A method for providing an electrochemical sensor, comprising the steps of:
providing an insulator;
depositing an electrode on the insulator;
placing an electrolytic material in contact with the electrode for providing an electrical connection;
placing a reservoir containing electrolyte solution in contact with the electrolytic material for hydrating the elec trolytic material placing a cooling and heating element in a hole located in the insulator and spaced apart from the electrode; and adjusting a temperature of the sensor with the cooling and heating element, wherein the cooling and heating element is a Peltier cooling and heating element.

18. The method according to claim 17, further comprising the step of placing a heat sink in communication with the cooling and heating element for removing heat from the sensor.

* * * * *